United States Patent
Moumene et al.

(10) Patent No.: US 9,445,844 B2
(45) Date of Patent: Sep. 20, 2016

(54) COMPOSITE MATERIAL POSTERIOR DYNAMIC STABILIZATION SPRING ROD

(75) Inventors: Missoum Moumene, Raynham, MA (US); Jonathan Fanger, Raynham, MA (US); Kevin Flaherty, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 340 days.

(21) Appl. No.: 12/730,473

(22) Filed: Mar. 24, 2010

(65) Prior Publication Data

US 2011/0238119 A1  Sep. 29, 2011

(51) Int. Cl.
*A61B 17/70* (2006.01)
(52) U.S. Cl.
CPC ....... *A61B 17/7011* (2013.01); *A61B 17/7028* (2013.01)
(58) Field of Classification Search
CPC ..................................... A61B 17/70–17/7046
USPC .......... 606/254–263, 246, 264–279; 428/188
See application file for complete search history.

(56) References Cited

U.S. PATENT DOCUMENTS

| | | | |
|---|---|---|---|
| 3,992,725 A * | 11/1976 | Homsy | 424/423 |
| 4,512,038 A * | 4/1985 | Alexander et al. | 623/23.75 |
| 4,648,388 A | 3/1987 | Steffee | |
| 4,743,260 A | 5/1988 | Burton | |
| 4,854,304 A | 8/1989 | Zielke | |
| 5,002,542 A | 3/1991 | Frigg | |
| 5,034,011 A | 7/1991 | Howland | |
| 5,092,866 A | 3/1992 | Breard | |
| 5,180,393 A | 1/1993 | Commarmond | |
| 5,181,930 A | 1/1993 | Dumbleton | |
| 5,207,678 A | 5/1993 | Harms | |
| 5,217,461 A | 6/1993 | Asher | |
| 5,217,497 A | 6/1993 | Mehdian | |
| 5,282,863 A | 2/1994 | Burton | |
| 5,344,422 A | 9/1994 | Frigg | |
| 5,360,431 A | 11/1994 | Puno | |

(Continued)

FOREIGN PATENT DOCUMENTS

| | | |
|---|---|---|
| EP | 46518 | 7/1983 |
| EP | 470660 | 7/1995 |

(Continued)

OTHER PUBLICATIONS

Betz, "Compairson of Anterior and Posterior Instrumentation for Correction of Adolsecent Thoracic Idiipathic Scoliosis", Spine, Feb. 1, 1999, vol. 24, Issue 3, pp. 225-239.

(Continued)

*Primary Examiner* — Jan Christopher Merene
*Assistant Examiner* — Steven Cotroneo (57) ABSTRACT

The present invention provides a Posterior Dynamic Stabilization (PDS) device that allows elongation, which is a critical requirement for a PDS device as it allows pedicles to travel naturally in flexion, extension, and lateral bending of the spine. This interpedicular travel preserves a more natural center of rotation unlike other PDS devices that simply allow bending. In particular, the invention involves a PDS spring rod, wherein the helix is created with composite flow molding (CFM) technology and comprises a polymer matrix reinforced with continuous carbon fibers, wherein the fibers are oriented substantially parallel to the centerline of the helix, thereby creating a high strength spring.

13 Claims, 9 Drawing Sheets

(56) References Cited

U.S. PATENT DOCUMENTS

| | | |
|---|---|---|
| 5,375,823 A | 12/1994 | Navas |
| 5,387,213 A | 2/1995 | Breard |
| 5,403,314 A | 4/1995 | Currier |
| 5,415,661 A | 5/1995 | Holmes |
| 5,423,816 A | 6/1995 | Lin |
| 5,429,639 A | 7/1995 | Judet |
| 5,474,555 A | 12/1995 | Puno |
| 5,486,174 A | 1/1996 | Fournet-Fayard |
| 5,496,321 A | 3/1996 | Puno |
| 5,520,689 A | 5/1996 | Schlapfer |
| 5,540,688 A | 7/1996 | Navas |
| 5,540,689 A | 7/1996 | Sanders |
| 5,562,660 A | 10/1996 | Grob |
| 5,562,663 A | 10/1996 | Wisnewski |
| 5,562,737 A | 10/1996 | Graf |
| 5,630,817 A | 5/1997 | Rokegem |
| 5,643,260 A | 7/1997 | Doherty |
| 5,658,286 A | 8/1997 | Sava |
| 5,672,175 A | 9/1997 | Martin |
| 5,672,176 A | 9/1997 | Biedermann |
| 5,683,390 A | 11/1997 | Metz-Stavenhagen |
| 5,702,395 A | 12/1997 | Hopf |
| 5,704,936 A | 1/1998 | Mazel |
| 5,704,937 A | 1/1998 | Martin |
| 5,728,098 A | 3/1998 | Sherman |
| 5,733,284 A | 3/1998 | Martin |
| 5,738,685 A | 4/1998 | Halm |
| 5,782,833 A | 7/1998 | Haider |
| 5,797,910 A | 8/1998 | Martin |
| 5,851,006 A | 12/1998 | Spillner |
| 5,879,350 A | 3/1999 | Sherman |
| RE36,221 E | 6/1999 | Breard |
| 5,954,725 A | 9/1999 | Sherman |
| 5,961,516 A | 10/1999 | Graf |
| 6,004,349 A | 12/1999 | Jackson |
| 6,022,350 A | 2/2000 | Ganem |
| 6,053,917 A | 4/2000 | Sherman |
| 6,063,090 A | 5/2000 | Schlapfer |
| 6,077,262 A | 6/2000 | Schlapfer |
| 6,083,226 A | 7/2000 | Fiz |
| 6,099,528 A | 8/2000 | Saurat |
| 6,102,912 A | 8/2000 | Cazin |
| 6,139,549 A | 10/2000 | Keller |
| 6,224,598 B1 | 5/2001 | Jackson |
| 6,241,730 B1* | 6/2001 | Alby ............. A61B 17/7007 403/120 |
| 6,248,105 B1 | 6/2001 | Schläpfer |
| 6,251,112 B1 | 6/2001 | Jackson |
| 6,267,764 B1 | 7/2001 | Elberg |
| 6,273,888 B1 | 8/2001 | Justis |
| 6,293,949 B1 | 9/2001 | Justis |
| 6,302,888 B1 | 10/2001 | Mellinger |
| 6,361,535 B2 | 3/2002 | Jackson |
| 6,371,957 B1 | 4/2002 | Amrein |
| 6,379,356 B1 | 4/2002 | Jackson |
| 6,402,750 B1 | 6/2002 | Atkinson |
| 6,402,752 B2 | 6/2002 | Schäffler-Wachter |
| 6,440,132 B1 | 8/2002 | Jackson |
| 6,471,705 B1 | 10/2002 | Biedermann |
| 6,485,491 B1 | 11/2002 | Farris |
| 6,520,963 B1 | 2/2003 | McKinley |
| 6,540,749 B2 | 4/2003 | Schäfer |
| 6,554,831 B1 | 4/2003 | Rivard |
| 6,595,993 B2 | 7/2003 | Donno |
| 6,626,908 B2 | 9/2003 | Cooper |
| 6,641,586 B2 | 11/2003 | Varieur |
| 6,645,207 B2 | 11/2003 | Dixon |
| 6,652,526 B1 | 11/2003 | Arafiles |
| 6,695,843 B2 | 2/2004 | Biedermann |
| 6,723,100 B2 | 4/2004 | Biedermann |
| 6,726,687 B2 | 4/2004 | Jackson |
| 6,730,089 B2 | 5/2004 | Jackson |
| 6,755,829 B1 | 6/2004 | Bono |
| 6,761,719 B2 | 7/2004 | Justis |
| 6,783,527 B2 | 8/2004 | Drewry |
| 6,786,903 B2 | 9/2004 | Lin |
| 6,796,984 B2 | 9/2004 | Soubeiran |
| 6,835,205 B2 | 12/2004 | Atkinson |
| 6,843,791 B2 | 1/2005 | Serhan |
| 6,896,677 B1 | 5/2005 | Lin |
| 6,905,500 B2 | 6/2005 | Jeon |
| 6,918,911 B2 | 7/2005 | Biedermann |
| 6,966,910 B2 | 11/2005 | Ritland |
| 6,986,771 B2 | 1/2006 | Paul |
| 6,989,011 B2 | 1/2006 | Paul |
| 6,997,927 B2 | 2/2006 | Jackson |
| 7,018,378 B2 | 3/2006 | Biedermann |
| 7,022,122 B2 | 4/2006 | Amrein |
| 7,029,475 B2 | 4/2006 | Panjabi |
| 7,125,410 B2 | 10/2006 | Freudiger |
| 7,137,985 B2 | 11/2006 | Jahng |
| 7,156,850 B2 | 1/2007 | Kim |
| 7,175,622 B2 | 2/2007 | Farris |
| 7,179,261 B2 | 2/2007 | Sicvol |
| 7,204,838 B2 | 4/2007 | Jackson |
| 7,211,086 B2 | 5/2007 | Biedermann |
| 7,261,714 B2 | 8/2007 | Richelsoph |
| 7,326,210 B2 | 2/2008 | Jahng |
| 7,329,258 B2 | 2/2008 | Studer |
| 7,335,200 B2 | 2/2008 | Carli |
| 7,419,714 B1 | 9/2008 | Magerl |
| 7,553,320 B2 | 6/2009 | Molz, IV |
| 7,556,639 B2 | 7/2009 | Rothman |
| 7,621,912 B2 | 11/2009 | Harms |
| 7,621,940 B2 | 11/2009 | Harms |
| 7,632,292 B2 | 12/2009 | Sengupta |
| 7,641,673 B2 | 1/2010 | Le Couedic |
| 7,651,515 B2 | 1/2010 | Mack |
| 7,708,762 B2 | 5/2010 | McCarthy |
| 7,713,287 B2 | 5/2010 | Timm |
| 7,717,941 B2 | 5/2010 | Petit |
| 7,722,649 B2 | 5/2010 | Biedermann |
| 7,727,258 B2 | 6/2010 | Graf |
| 7,763,052 B2 | 7/2010 | Jahng |
| 7,776,071 B2 | 8/2010 | Fortin |
| 7,776,075 B2 | 8/2010 | Bruneau |
| 7,794,476 B2 | 9/2010 | Wisnewski |
| 7,811,309 B2 | 10/2010 | Timm |
| 7,815,665 B2 | 10/2010 | Jahng |
| 7,833,256 B2 | 11/2010 | Biedermann |
| 7,846,187 B2 | 12/2010 | Jackson |
| 7,862,586 B2 | 1/2011 | Malek |
| 7,942,907 B2 | 5/2011 | Richelsoph |
| 7,988,710 B2 | 8/2011 | Jahng |
| 7,993,370 B2 | 8/2011 | Jahng |
| 8,012,178 B2 | 9/2011 | Hartmann |
| 8,157,843 B2 | 4/2012 | Biedermann |
| 8,221,467 B2 | 7/2012 | Butler |
| 8,221,472 B2 | 7/2012 | Peterson |
| 8,241,362 B2 | 8/2012 | Voorhies |
| 8,911,484 B2 | 12/2014 | Lei |
| 2002/0058942 A1 | 5/2002 | Biedermann |
| 2002/0072751 A1 | 6/2002 | Jackson |
| 2002/0082602 A1 | 6/2002 | Biedermann |
| 2002/0133155 A1 | 9/2002 | Ferree |
| 2002/0133159 A1 | 9/2002 | Jackson |
| 2003/0009226 A1 | 1/2003 | Graf |
| 2003/0041441 A1 | 3/2003 | Lin |
| 2003/0055426 A1 | 3/2003 | Carbone |
| 2003/0055427 A1 | 3/2003 | Graf |
| 2003/0083657 A1 | 5/2003 | Drewry |
| 2003/0100896 A1 | 5/2003 | Biedermann |
| 2003/0109880 A1 | 6/2003 | Shirado |
| 2003/0125741 A1 | 7/2003 | Biedermann |
| 2003/0149431 A1 | 8/2003 | Varieur |
| 2003/0153912 A1 | 8/2003 | Graf |
| 2003/0171749 A1 | 9/2003 | Le Couedic |
| 2003/0191470 A1 | 10/2003 | Ritland |
| 2003/0220642 A1 | 11/2003 | Freudiger |
| 2003/0220643 A1* | 11/2003 | Ferree ............. 606/61 |
| 2004/0002708 A1 | 1/2004 | Ritland |
| 2004/0049189 A1 | 3/2004 | Le Couedic |
| 2004/0049190 A1 | 3/2004 | Biedermann |
| 2004/0068258 A1 | 4/2004 | Schlapfer |

(56) References Cited

U.S. PATENT DOCUMENTS

| | | |
|---|---|---|
| 2004/0073215 A1 | 4/2004 | Carli |
| 2004/0097926 A1 | 5/2004 | Kim |
| 2004/0097933 A1 | 5/2004 | Lourdel |
| 2004/0106921 A1 | 6/2004 | Cheung |
| 2004/0116927 A1 | 6/2004 | Graf |
| 2004/0143264 A1 | 7/2004 | McAfee |
| 2004/0167523 A1 | 8/2004 | Jackson |
| 2004/0186474 A1 | 9/2004 | Matthis |
| 2004/0186478 A1 | 9/2004 | Jackson |
| 2004/0215191 A1 | 10/2004 | Kitchen |
| 2004/0215192 A1 | 10/2004 | Justis |
| 2004/0225289 A1 | 11/2004 | Biedermann |
| 2004/0230191 A1 | 11/2004 | Frey |
| 2004/0230192 A1 | 11/2004 | Graf |
| 2004/0236327 A1 | 11/2004 | Paul |
| 2004/0236328 A1 | 11/2004 | Paul |
| 2004/0236329 A1 | 11/2004 | Panjabi |
| 2004/0260284 A1 | 12/2004 | Parker |
| 2004/0264386 A1 | 12/2004 | Ha |
| 2004/0267260 A1 | 12/2004 | Mack |
| 2005/0027292 A1 | 2/2005 | Bernard |
| 2005/0033295 A1 | 2/2005 | Wisnewski |
| 2005/0038432 A1 | 2/2005 | Shaolian |
| 2005/0049708 A1 | 3/2005 | Atkinson |
| 2005/0056979 A1 | 3/2005 | Studer |
| 2005/0065514 A1* | 3/2005 | Studer ............... 606/61 |
| 2005/0065516 A1 | 3/2005 | Jahng |
| 2005/0080414 A1 | 4/2005 | Keyer |
| 2005/0085814 A1 | 4/2005 | Sherman |
| 2005/0085815 A1 | 4/2005 | Harms |
| 2005/0113927 A1 | 5/2005 | Malek |
| 2005/0124991 A1* | 6/2005 | Jahng ............... 606/61 |
| 2005/0129499 A1 | 6/2005 | Morris |
| 2005/0131407 A1 | 6/2005 | Sicvol |
| 2005/0131421 A1 | 6/2005 | Anderson |
| 2005/0131422 A1 | 6/2005 | Anderson |
| 2005/0143737 A1 | 6/2005 | Pafford |
| 2005/0143823 A1 | 6/2005 | Boyd |
| 2005/0149020 A1 | 7/2005 | Jahng |
| 2005/0154389 A1 | 7/2005 | Selover |
| 2005/0154390 A1 | 7/2005 | Biedermann |
| 2005/0165396 A1 | 7/2005 | Fortin |
| 2005/0171543 A1 | 8/2005 | Timm |
| 2005/0177156 A1* | 8/2005 | Timm et al. ............... 606/61 |
| 2005/0177157 A1 | 8/2005 | Jahng |
| 2005/0177164 A1 | 8/2005 | Walters |
| 2005/0182400 A1 | 8/2005 | White |
| 2005/0182401 A1 | 8/2005 | Timm |
| 2005/0182409 A1 | 8/2005 | Callahan |
| 2005/0187549 A1 | 8/2005 | Jackson |
| 2005/0192589 A1 | 9/2005 | Raymond |
| 2005/0202519 A1 | 9/2005 | Barthe |
| 2005/0203511 A1 | 9/2005 | Wilson-MacDonald |
| 2005/0203513 A1 | 9/2005 | Jahng |
| 2005/0203514 A1 | 9/2005 | Jahng |
| 2005/0203516 A1 | 9/2005 | Biedermann |
| 2005/0203517 A1 | 9/2005 | Jahng |
| 2005/0203518 A1 | 9/2005 | Biedermann |
| 2005/0203519 A1 | 9/2005 | Harms |
| 2005/0215999 A1 | 9/2005 | Birkmeyer |
| 2005/0216003 A1 | 9/2005 | Biedermann |
| 2005/0222569 A1 | 10/2005 | Panjabi |
| 2005/0222659 A1 | 10/2005 | Olsen |
| 2005/0245930 A1 | 11/2005 | Timm |
| 2005/0261685 A1 | 11/2005 | Fortin |
| 2005/0261686 A1 | 11/2005 | Paul |
| 2005/0267471 A1 | 12/2005 | Biedermann |
| 2005/0277919 A1 | 12/2005 | Slivka |
| 2005/0277922 A1 | 12/2005 | Trieu |
| 2005/0288670 A1 | 12/2005 | Panjabi |
| 2005/0288672 A1 | 12/2005 | Ferree |
| 2006/0009768 A1 | 1/2006 | Ritland |
| 2006/0025767 A1 | 2/2006 | Khalili |
| 2006/0036240 A1 | 2/2006 | Colleran |
| 2006/0041259 A1 | 2/2006 | Paul |
| 2006/0064090 A1* | 3/2006 | Park ............... A61B 17/7005 606/250 |
| 2006/0084984 A1 | 4/2006 | Kim |
| 2006/0106380 A1 | 5/2006 | Colleran |
| 2006/0106381 A1 | 5/2006 | Ferree |
| 2006/0129147 A1 | 6/2006 | Biedermann |
| 2006/0142758 A1 | 6/2006 | Petit |
| 2006/0142760 A1 | 6/2006 | McDonnell |
| 2006/0149235 A1 | 7/2006 | Jackson |
| 2006/0149291 A1 | 7/2006 | Selover |
| 2006/0155279 A1 | 7/2006 | Ogilvie |
| 2006/0161152 A1 | 7/2006 | Ensign et al. |
| 2006/0184171 A1* | 8/2006 | Biedermann et al. ............ 606/61 |
| 2006/0189983 A1 | 8/2006 | Fallin |
| 2006/0189984 A1 | 8/2006 | Fallin |
| 2006/0195093 A1 | 8/2006 | Jahng |
| 2006/0201609 A1* | 9/2006 | Edwin ............... A61F 2/86 156/192 |
| 2006/0212033 A1 | 9/2006 | Rothman |
| 2006/0229607 A1 | 10/2006 | Brumfield |
| 2006/0229608 A1* | 10/2006 | Foster et al. ............... 606/61 |
| 2006/0229612 A1 | 10/2006 | Rothman |
| 2006/0240533 A1 | 10/2006 | Sengupta |
| 2006/0247632 A1 | 11/2006 | Winslow |
| 2006/0247637 A1 | 11/2006 | Colleran |
| 2006/0247638 A1 | 11/2006 | Trieu |
| 2006/0260483 A1 | 11/2006 | Hartmann |
| 2006/0264935 A1 | 11/2006 | White |
| 2006/0264937 A1 | 11/2006 | White |
| 2006/0265074 A1 | 11/2006 | Krishna |
| 2006/0282080 A1 | 12/2006 | Albert |
| 2007/0003598 A1 | 1/2007 | Trieu |
| 2007/0005063 A1 | 1/2007 | Bruneau |
| 2007/0016190 A1 | 1/2007 | Martinez |
| 2007/0016201 A1 | 1/2007 | Freudiger |
| 2007/0019808 A1 | 1/2007 | Gonzalez |
| 2007/0049937 A1 | 3/2007 | Matthis |
| 2007/0055241 A1 | 3/2007 | Matthis |
| 2007/0055244 A1 | 3/2007 | Jackson |
| 2007/0055247 A1 | 3/2007 | Jahng |
| 2007/0161992 A1* | 7/2007 | Kwak ............... A61B 17/7065 606/249 |
| 2007/0190230 A1 | 8/2007 | Trieu |
| 2007/0191832 A1 | 8/2007 | Trieu |
| 2007/0191841 A1 | 8/2007 | Justis |
| 2007/0198088 A1 | 8/2007 | Biedermann |
| 2007/0233064 A1 | 10/2007 | Holt |
| 2007/0233073 A1 | 10/2007 | Wisnewski |
| 2007/0233085 A1 | 10/2007 | Biedermann |
| 2007/0233097 A1 | 10/2007 | Anderson |
| 2007/0270814 A1 | 11/2007 | Lim |
| 2007/0270838 A1 | 11/2007 | Bruneau |
| 2007/0270843 A1 | 11/2007 | Matthis |
| 2007/0299445 A1* | 12/2007 | Shadduck ............... A61B 17/7011 606/86 A |
| 2008/0021469 A1 | 1/2008 | Holt |
| 2008/0033435 A1 | 2/2008 | Studer |
| 2008/0058809 A1 | 3/2008 | Graf |
| 2008/0140133 A1 | 6/2008 | Allard |
| 2008/0147122 A1 | 6/2008 | Jackson |
| 2008/0161853 A1 | 7/2008 | Arnold |
| 2008/0161863 A1 | 7/2008 | Arnold |
| 2008/0183213 A1 | 7/2008 | Veldman |
| 2008/0195105 A1 | 8/2008 | Sidebotham |
| 2008/0195153 A1 | 8/2008 | Thompson |
| 2008/0262552 A1* | 10/2008 | Kim ............... 606/276 |
| 2008/0312694 A1 | 12/2008 | Peterman |
| 2009/0005817 A1 | 1/2009 | Friedrich |
| 2009/0012562 A1 | 1/2009 | Hestad |
| 2009/0030464 A1 | 1/2009 | Hestad |
| 2009/0048631 A1 | 2/2009 | Bhatnagar |
| 2009/0062866 A1 | 3/2009 | Jackson |
| 2009/0099608 A1 | 4/2009 | Szczesny |
| 2009/0131981 A1 | 5/2009 | White |
| 2009/0155289 A1 | 6/2009 | Roberts |
| 2009/0163953 A1* | 6/2009 | Biedermann et al. ............ 606/254 |
| 2009/0204155 A1 | 8/2009 | Aschmann |
| 2009/0234388 A1 | 9/2009 | Patterson |
| 2009/0251573 A1 | 10/2009 | Toyoda |

(56) References Cited

U.S. PATENT DOCUMENTS

| | | |
|---|---|---|
| 2010/0042156 A1 | 2/2010 | Harms |
| 2010/0069962 A1 | 3/2010 | Harms |
| 2010/0069964 A1 | 3/2010 | Lechmann |
| 2010/0114169 A1 | 5/2010 | Le Couedic |
| 2010/0114173 A1 | 5/2010 | Le Couedic |
| 2010/0174317 A1 | 7/2010 | Timm |
| 2010/0204736 A1 | 8/2010 | Biedermann |
| 2011/0054534 A1 | 3/2011 | Biedermann |
| 2012/0265247 A1 | 10/2012 | Biedermann |
| 2014/0031868 A1 | 1/2014 | Biedermann |

FOREIGN PATENT DOCUMENTS

| | | |
|---|---|---|
| EP | 667127 | 8/1995 |
| EP | 677277 | 2/1996 |
| EP | 669109 | 5/1999 |
| EP | 1579816 | 6/2013 |
| FR | 2717370 | 9/1995 |
| GB | 382307 | 5/2003 |
| WO | WO 9501132 | 1/1995 |
| WO | WO 9505783 | 3/1995 |
| WO | WO 9641582 | 12/1996 |
| WO | WO 0145576 | 6/2001 |
| WO | WO 0156489 | 8/2001 |
| WO | WO 03047441 | 6/2003 |
| WO | WO 2005027761 | 3/2005 |
| WO | WO 2005030031 | 4/2005 |
| WO | WO 2005039454 | 7/2005 |
| WO | WO 2005044117 | 8/2005 |
| WO | WO 2005094704 | 10/2005 |
| WO | WO 2006079531 | 8/2006 |
| WO | WO 2006063107 | 12/2006 |

OTHER PUBLICATIONS

Desroches "Biomechanical modeling of anterior spine instrumentation in AIS", STUD Health Technol Inform, 2006, vol. 123, pp. 415-418—abstract.

Hefti, "Repair of lumbar spondylolysis with a hook-screw", Int Orthop., 1992, vol. 16, Issue 1, pp. 81-85—abstract.

Nohara, "Biomechanical study of adjacent intervertebral motion after lumbar spinal fusion and flexible stabilization using polyethylene-terephthalate bands", J Spinal Discord Tech, Jun. 2004, vol. 17, Issue 3, pp. 215-219—abstract.

Poulin, "Biomechanical modeling of instrumentation for the scoliotic spine using flexible elements:a feasibility study", ANN CHIR, 1998, 52(8), pp. 761-767—abstract.

Sanders, "A Preliminary Investigation of Shape Memory Alloys in the Surgical Correctionof Scoliosis", Spine, Sep. 15, 1993, vol. 18, Issue 12, pp. 1640-1646.

Smith, "Does Instrumented Anterior Scoliosis Surgery Lead to Pyphosis, Pseudarthrosis, or Inadequate Correction in Adults", Spine, Mar. 1, 2002, vol. 27, Issue 5, pp. 529-534.

Teitelbaum, "New Percutaneously Inserted Spinal Fixation System", Spine, Mar. 11, 2004, vol. 29, Issue 6, pp. 703-709.

Veldhuizen, "A Scoliosis Correction Device Based on Memory Metal", Med. Eng. Phys., 1997, vol. 19, pp. 171-179, Elsevier Science Ltd.

\* cited by examiner

| Model | Wire Diameter, mm | Helix OD/ID, mm | Pitch, mm | N coils, # | Stiffness N/mm | Stress, MPa | Failure Stress, MPa |
|---|---|---|---|---|---|---|---|
| Regression /LOMM | 2.45 | 7.45/2.55 | 4 | 3 | 100.7 | 394.6 | 770 |
| FEA | 2.45 | 7.45/2.45 | 4 | 3 | 106.0 | 427/342 | 770 |
| Regression | 2.3 | 7.15/2.55 | 4 | 3 | 81.8 | 420.2 | 770 |
| Regression | 2.4 | 7.5/2.7 | 4 | 3 | 79.1 | 347.7 | 770 |
| Regression | 2.5 | 7.8/2.8 | 4 | 3 | 81.6 | 293.6 | 770 |

FIG. 8B

LOMM

COMPOSITE MATERIAL POSTERIOR DYNAMIC STABILIZATION SPRING ROD

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage that allow the joints to move or articulate relative to one another.

Diseased, degenerated, impaired, or otherwise painful facet joints and/or discs can require surgery to restore function to the three joint complex. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. These arches can articulate relative to one another to replace the articulating function of the facet joints. One drawback to current articulating facet replacement devices, however, is that they require the facet joints to be resected, which entails an invasive surgery. Moreover, alignment of the articulating surfaces with one another can be challenging.

Accordingly, there remains a need for improved systems and methods that are adapted to mimic the natural function of the facet joints.

Traditional spine fusion may result in early degeneration at adjacent spine levels due to increased loading and compensation. This may result in subsequent surgeries to fuse additional levels. Stabilization using more dynamic rods with traditional pedicle screw instrumentation may improve surgical outcomes and reduce additional surgeries for adjacent level degeneration.

U.S. Pat. No. 7,419,714 (Magerl) discloses a composite of polymer or ceramic material having reinforcing fibers. The composite is used to manufacture medical implants such as osteosynthesis plates, endoprostheses, screw coupling elements, surgical instruments, and similar components. The reinforcing fibers and fibrous parts are made from a material that absorbs X-rays so that it can be seen during X-ray examination. Magerl proposes that the composite comprises a polymer or ceramic material with a high fiber percentage, primarily using continuous, long or short fibers, wherein at least a small percentage of fibers or fibrous parts consist of a material with a high X-ray absorption. Despite a very high percentage of continuous fibers, the volume percentage of residual material can be retained, and the existing strength characteristics can be retained or even enhanced through the sole replacement of otherwise present fibers with fibers consisting of a material with a high X-ray absorption. In one embodiment, it is proposed that the composite consist of carbon fiber-reinforced PAEK (poly-aryl-ether-ketone) and a percentage of fibers made out of a material with a high X-ray absorption. This makes it a material with a special compatibility, high strength and the visibility necessary for X-ray diagnostics. Optimal strength levels can be achieved by designing the carbon fibers and fibers made out of a material with a higher X-ray absorption as continuous fibers and/or fibers with a length exceeding 3 mm. To enable a transfer of force between the fibers and the other material of the composite, i.e., to also ensure an optimal strength at a high volume density of fibers, the selected fibers should be enveloped on the surface by the matrix material both in the preform and in the finished component.

SUMMARY OF THE INVENTION

The present invention provides a posterior dynamic stabilization (PDS) device that allows elongation, which is a critical requirement for a PDS device, as it allows pedicles to travel naturally during the flexion, extension, and lateral bending of the spine. This interpedicular travel preserves a more natural center of rotation, and so differentiates the PDS device of the present invention from other PDS devices that simply allow bending. In preferred embodiments, the invention involves a PDS spring rod having a helix created with composite flow molding (CFM) technology. The helix is preferably made of a polymer matrix reinforced with continuous carbon fibers, wherein the fibers are oriented substantially parallel to the centerline of the helix, thereby creating a high strength spring.

The device of the present invention provides superior yield strength, ultimate strength and fatigue properties. The device will allow greater elongation than PDS devices made from traditional materials. The composite material provides the PDS device of the present invention with high flexibility and strength, whereas conventional PDS systems that use metallic springs do not allow much elongation prior to yielding. It is further believed that the composite spring rod of the present invention will have better imaging capabilities than conventional metallic rods because it is an inherently radiolucent polymer.

Therefore, in accordance with the present invention, there is provided a posterior dynamic spinal stabilization system, comprising:
  a) a rod having a first end portion, an intermediate portion having a substantially helical portion having a centerline, and a second end portion,
  b) a first bone anchor having i) a shank and ii) a rod-receiving portion mated to the first end portion of the rod,
  c) a second bone anchor having i) a shank and ii) a rod-receiving portion mated to the second end portion of the rod,
  wherein the substantially helical portion of the rod comprises a polymer matrix reinforced with continuous fibers, wherein the fibers are oriented substantially parallel to the centerline of the substantially helical portion.

DETAILED DESCRIPTION OF THE INVENTION

Figure 6:
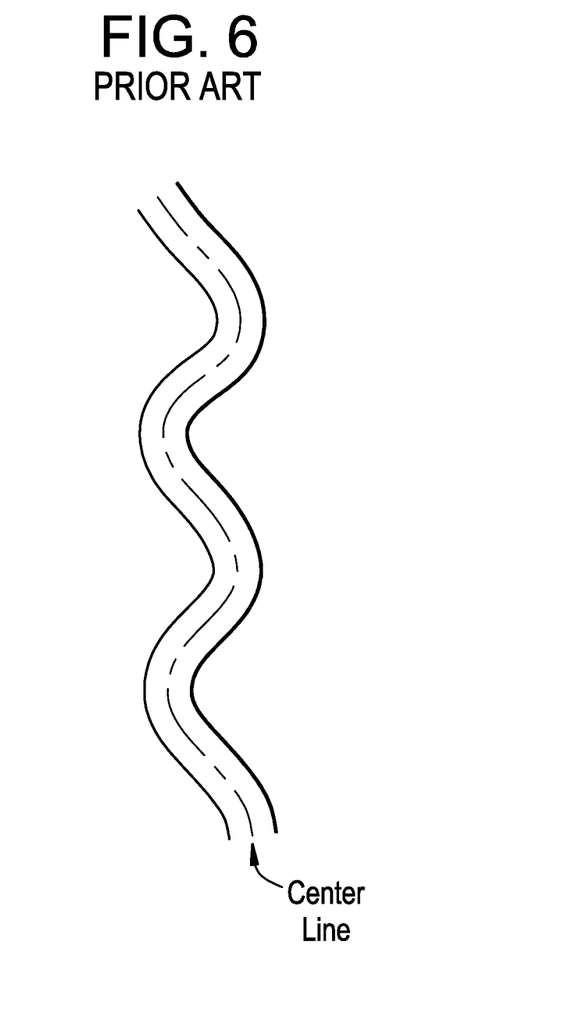
FIG. 6 discloses a centerline of a helix.

For the purposes of the present invention, and now referring to FIG. 6, the "centerline" of a helix is the dotted line shown in the helix of FIG. 6. It is the line that is the sum of the centerpoints created by the sequential transverse cross-sections of the helix.

The present invention involves a spinal implant device for posterior dynamic stabilization that includes a helical spring device constructed from a composite material. In a preferred embodiment of the invention, the helical spring is molded from a cylinder of an endless fiber reinforced thermoplastic, which will provide the device with excellent fatigue, flexural, shear, and tensile strengths. The cylinder of endless fiber reinforced thermoplastic is preferably made by a pultrusion process that creates endless fibers embedded in a polymer matrix and running parallel to the longitudinal axis of the cylinder. This molding process combined with the endless fibers results in a spring with high strength, since the fibers are oriented to run substantially parallel to the centerline of the helix and never protrude from its surface.

Figure 1A:
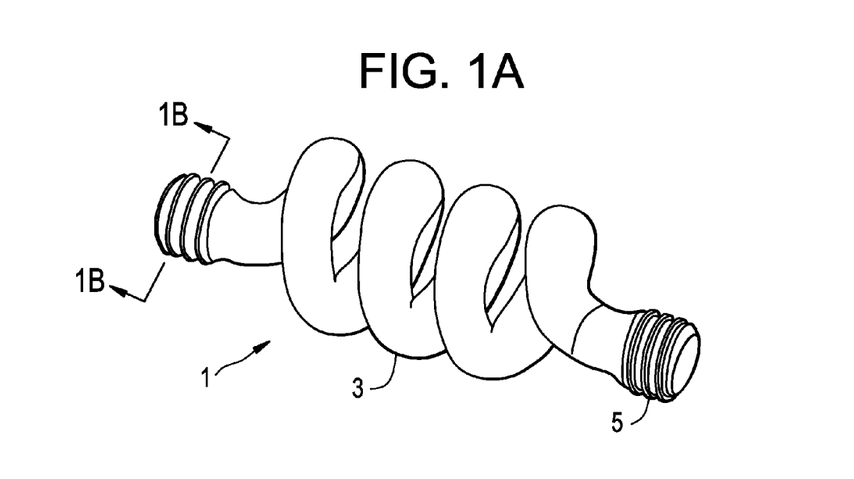
FIG. 1a discloses a perspective view of an intermediate portion of the rod of the present invention, wherein the intermediate portion comprises threaded ends.

Now referring to FIG. 1a, there is provided a component that represents an intermediate portion 1 of the rod of the present invention, wherein the intermediate portion comprises a helical mid portion 3 and threaded ends 5. The entire intermediate portion of the rod comprises (and preferably consists essentially of) a polymer matrix reinforced with continuous carbon fibers. In the helical mid portion thereof, the continuous carbon fibers are oriented parallel to the centerline of the helix substantially throughout the helix, thereby creating a high strength spring.

Therefore, in accordance with the present invention, there is provided a posterior dynamic spinal stabilization rod having a first end portion, an intermediate portion having a substantially helical portion having a centerline, and a second end portion, wherein the substantially helical portion of the rod comprises a polymer matrix reinforced with continuous fibers, wherein the continuous fibers are oriented substantially parallel to the centerline of the helical portion.

Figure 1B:
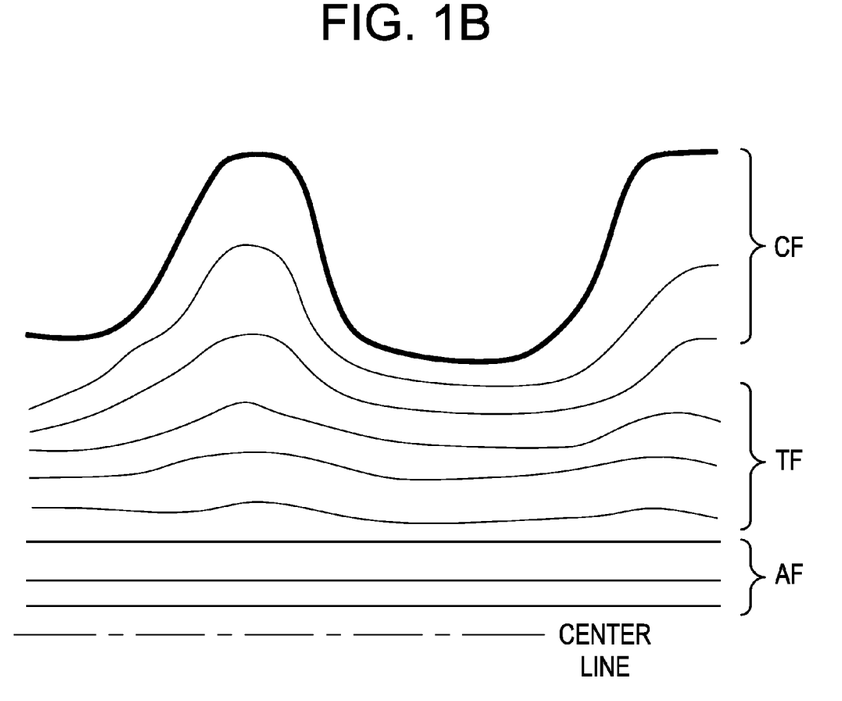
FIG. 1b discloses a semi-cross-section of the rod of FIG. 1a taken across a thread.

As shown in FIG. 1a, the ends of the intermediate portion may have threads. If threads are present, the fibers in the thread region can advantageously be oriented along the contour of the thread (i.e., parallel to the contour surface) such that the threads possess a high strength. In the threaded end regions, the deeper continuous carbon fibers are oriented parallel to the longitudinal axis of this region, while the more superficial continuous carbon fibers are oriented as waves along the profile of the thread, thereby creating threads of high strength. Now referring to FIG. 1b, there is provided a diagram of such fiber preferred orientation. This image illustrates deep axial fibers (AF): transition zone fibers (TZF); and then superficial fibers oriented along the contour (CF) to give the threads high strength. The present invention takes advantage of this graded orientation for PDS spring rod applications.

Figure 2:
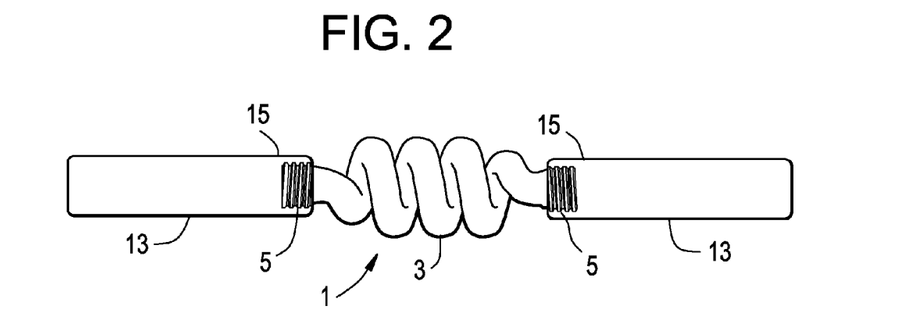
FIG. 2 discloses a rod of the present invention, comprising the intermediate portion of FIG. 1 threaded onto a pair of cylindrical end portions.

Now referring to FIG. 2, there is provided a rod 11 of the present invention, comprising the intermediate portion 1 of FIG. 1 threaded onto a pair of cylindrical end portions 13. The intermediate portion 1 of the modular rod comprises a helical mid portion 3 and threaded ends 5. The first and second cylindrical end portions 13 of the modular rod each have threaded inner ends 15. The threaded inner ends of the first and second cylindrical end portions of the modular rod threadably mate with respective threaded ends of the intermediate portion of the modular rod.

Therefore, in accordance with the present invention, there is provided a posterior dynamic spinal stabilization system comprising:
 a) a modular rod having a first end portion, an intermediate portion, and a second end portion,
 b) a first bone anchor having i) a shank and ii) a rod-receiving portion mated to the first end portion of the rod,
 c) a second bone anchor having i) a shank and ii) a rod-receiving portion mated to the second end portion of the rod,
wherein the intermediate portion of the modular rod comprises a helical mid portion and first and second threaded ends, wherein the first and second end portions of the modular rod each have threaded inner ends, wherein the threaded inner ends of the first and second end portions of the modular rod threadably mate with the first and second threaded ends of the intermediate portion of the modular rod.

In some embodiments, the molded threads 5 at the ends of the intermediate portion are threadably attached to threaded metallic inner ends 15. Preferably, these metallic inner ends are titanium. In some embodiments, a tapered thread or other interference feature can be used to prevent the mated end components from loosening.

Figure 3:
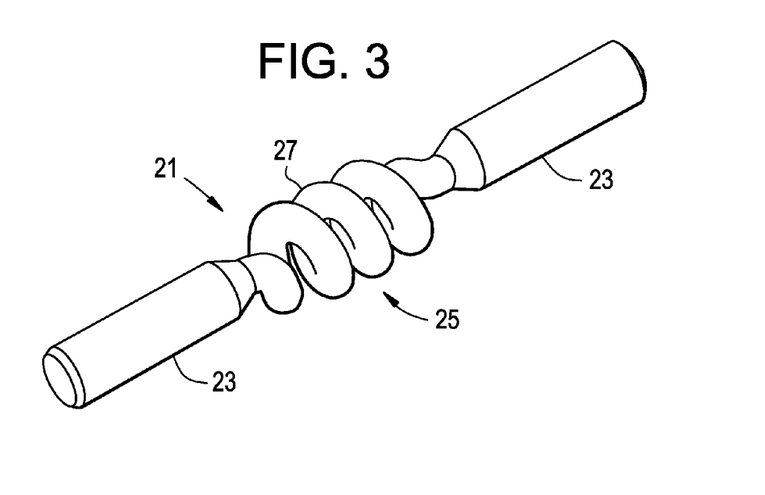
FIG. 3 discloses a unitary rod of the present invention.

Now referring to FIG. 3, in this embodiment, there is provided a unitary rod 21 of the present invention. The rod has first and second cylindrical end portions 23, and an intermediate portion 25 therebetween that comprises a substantially helical mid portion 27.

Preferably, the end portions of the rod are molded into a substantially cylindrical shape. These cylindrical end portions can then be attached to a pair of conventional pedicle screws.

When, as here, the intermediate and end portions are integral, they are made of the same composite material. Alternatively, they can be made from different materials, e.g., from metallic cylindrical sections and composite spring sections, as in FIG. 2.

Figure 4:
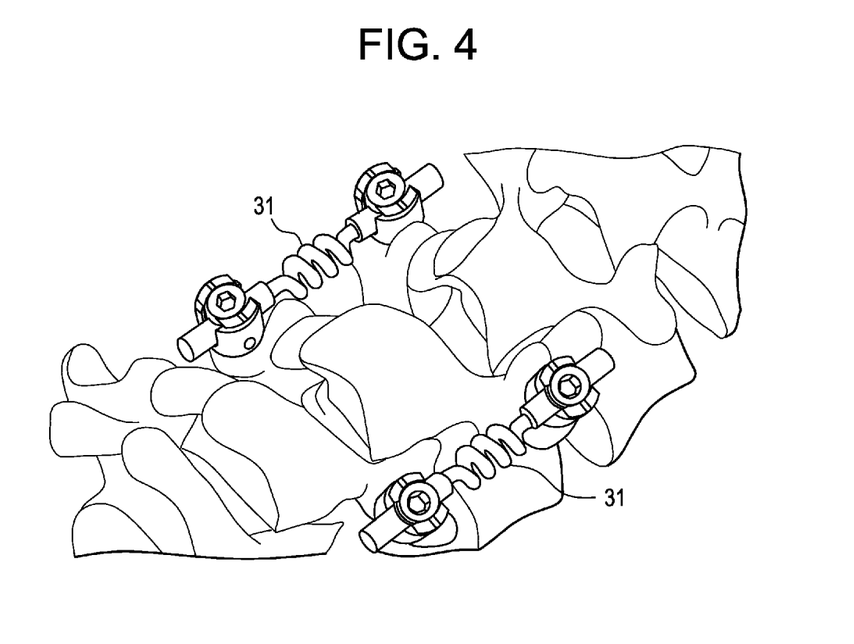
FIG. 4 discloses a pair of PDS devices of the present invention implanted in a human spine.

Now referring to FIG. 4, there is disclosed an implanted PDS device 31 of the present invention (comprising the rod attached to a pair of pedicle screws) providing dynamic stabilization to the spine. Although the device is shown in a single level application, it may also be used in multi-level procedures as well. Conventional techniques for implanting PDS rods and screws may be used. In FIG. 4, the pedicle screws attach to the end portions of the device of the present invention. In other embodiments (not shown), at least one of the pedicle screws may attach to a helical portion of the device.

Figure 5:
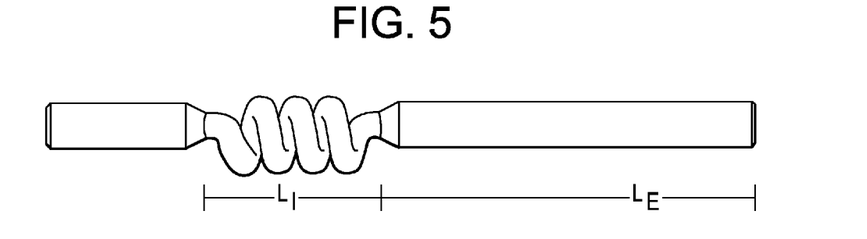
FIG. 5 discloses a unitary rod of the present invention having an elongated end portion suitable for topping off.

The "topping off" indication for early degenerative disc disease and stenosis may be a commercially valuable application for PDS devices. It is believed that the device of the present invention would also be suitable as a topping off solution to prevent overloading of the adjacent disc. Now referring to FIG. 5, the composite rod may be made with one or more elongated end portions, wherein the length $L_E$ of the elongated end portion is at least 150% of the length $L_I$ of the intermediate portion. Such a rod may be advantageously used in topping off applications, such as in DDD or stenosis applications. As shown in FIG. 5, the intermediate portion may be connected to the end portion by a transition region, in this case a frustoconical transition region.

In some embodiments (as in FIG. 5), a preferred "topping off" device comprises first and second end portions, wherein the first end portion is longer than the second end portion. Preferably, the first end portion is at least twice as long as the second end portion.

In some embodiments (not shown), the rod may possess more than one helical sections.

The CFM process can be used to create components with varying levels of carbon fiber. Carbon fiber content may typically be between 10 vol % and 70 vol %. The thermoplastic material may be polyarylethyl ketone (PAEK) or any other biocompatible polymer. The carbon content and/or thermoplastic content may be altered to create springs with varying stiffnesses for different clinical applications.

In some embodiments, at least 50 vol % of the continuous fibers are at least 3 mm in length. More preferably, at least 50 vol % of the continuous fibers are at least 10 mm in length. More preferably, at least 50 vol % of the continuous fibers run from one end of the intermediate portion of the rod to the other end.

When a polymer is chosen as a material of construction, the polymer is preferably selected from the group consisting of polycarbonates, polyesters, (particularly aromatic esters such as polyalkylene terephthalates, polyamides; polyalkenes; poly(vinyl fluoride); PTFE; polyarylethyl ketone (PAEK); and mixtures thereof.

In some embodiments, at least a portion of the rod component is made from a composite comprising PAEK and carbon fiber. Composites comprising carbon fiber are advantageous in that they typically have a strength and stiffness that is superior to neat polymer materials such as a polyarylethyl ketone PAEK. In some embodiments, the rod is made from a polymer composite such as a polyether ketone ketone (PEKK)-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 40 vol % and 80 vol % (more preferably, between 50 vol % and 70 vol %) of the composite. In some embodiments, the polymer and carbon fibers are homogeneously extruded, with the fibers running parallel to the longitudinal axis of the extrudate. In others, the material is a laminate. In other embodiments, the longitudinal fibers are covered with a layer of braided fibers, with a braid angle between about 10 degrees and about 80 degrees, preferably about 45 degrees.

In especially preferred embodiments, the composite comprises:

a) 30-50% (more preferably, 40 vol %) polyarylethyl ketone (PAEK), and b) 50-70% (more preferably, about 60 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 30-50 vol % PAEK and 50-70 vol % carbon fiber. Still more preferably the composite comprises about 40 vol % PAEK and 60 vol % carbon fiber.

Preferred composite materials of the present invention can be obtained from Icotec AG, Industriestrasse 12, CH-9450 Altstatten, Switzerland.

Preferably, the substantially helical portion of the rod comprises a polymer matrix reinforced with continuous fibers, wherein the fibers are oriented substantially parallel to the centerline of the helix. Accordingly, the continuous fibers should never break the surface of the helix.

In some embodiments, a first portion of the fibers are carbon fibers and a second portion of the fibers are made of a material that is more x-ray opaque than carbon. In some embodiments, such fiber mixtures are selected from the disclosure in U.S. Pat. No. 7,419,714, the specification of which is incorporated by reference in its entirety. In some embodiments, the x-ray opaque fibers are selected from the group consisting of tantalum, tungsten, gold, platinum, and their oxides.

In some embodiments, the composite material comprising the polymer matrix and continuous carbon fiber is extruded to form a long cylinder, in which the fiber runs parallel to the longitudinal axis of the cylinder. The extruded cylinder is then molded under elevated temperature and pressure to form the desired shape.

In one prophetic method of making the present invention, first, a rod is made by pultrusion using carbon fiber reinforced PEEK with carbon fiber volume fraction of 60 to 65%. The rod is cut into blank whose volume is precisely equal to the volume of the final spring. The blank is heated in a chamber where the PEEK melts and wet-out the continuous fibers, minimizing voids. The blank is then transferred to a compression mold cavity where it is pressed to form the final spring with fiber orientation along the coil to enhance strength.

Figure 7A:
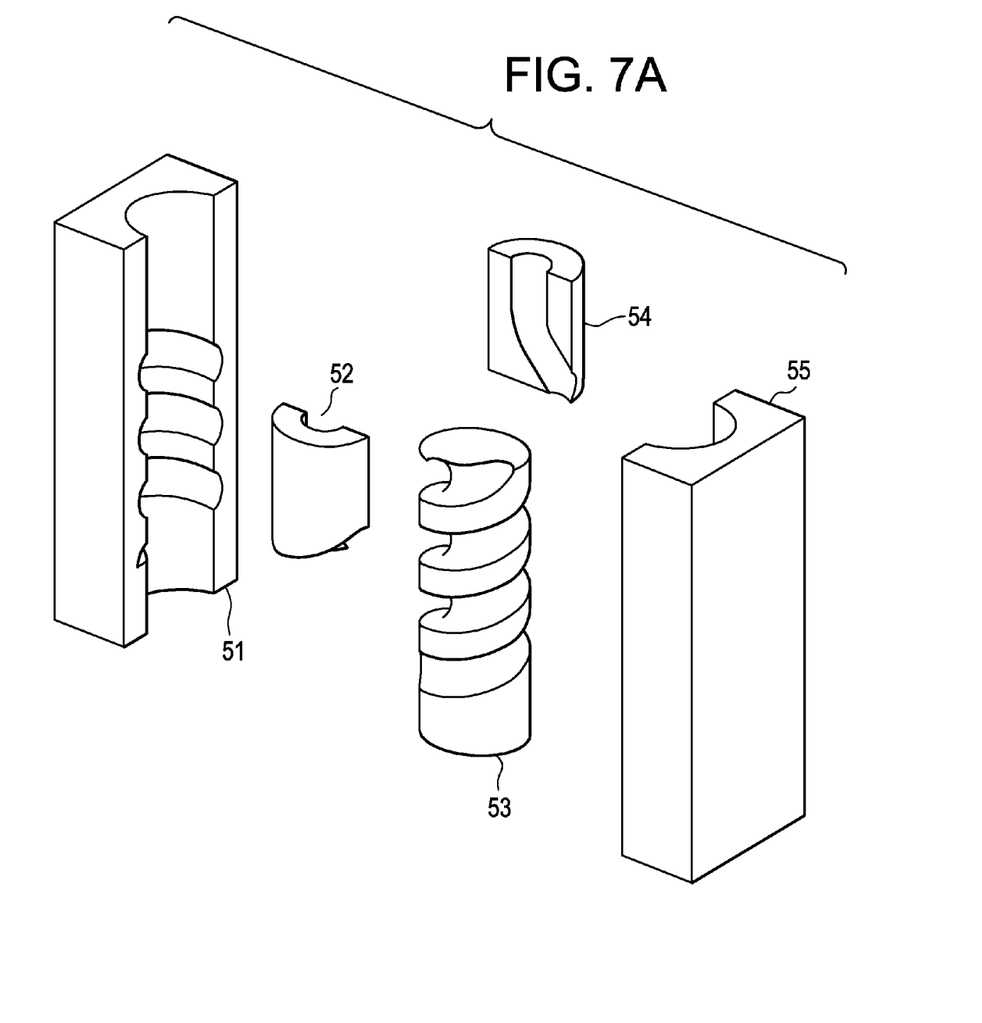
FIGS. 7a-7c disclose the construction of a mold of the present invention from multiple components.
Figure 7B:
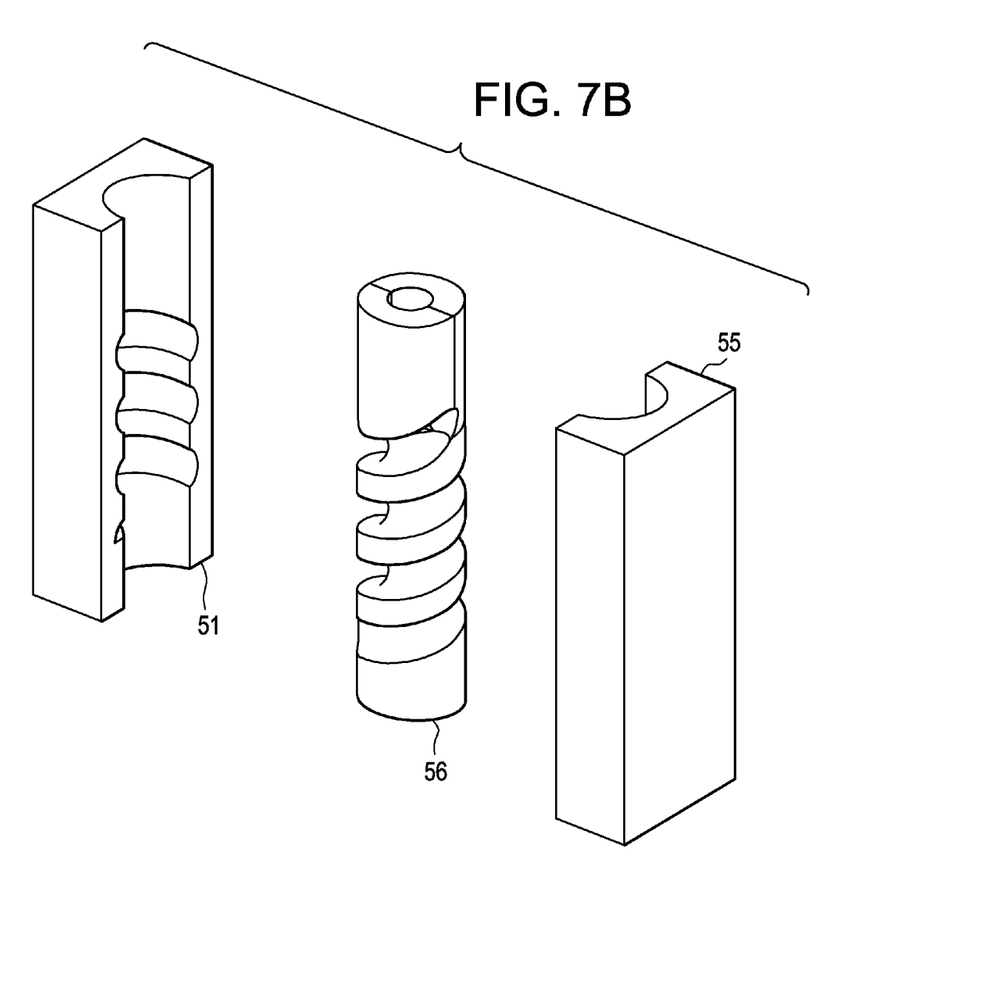
Figure 7C:
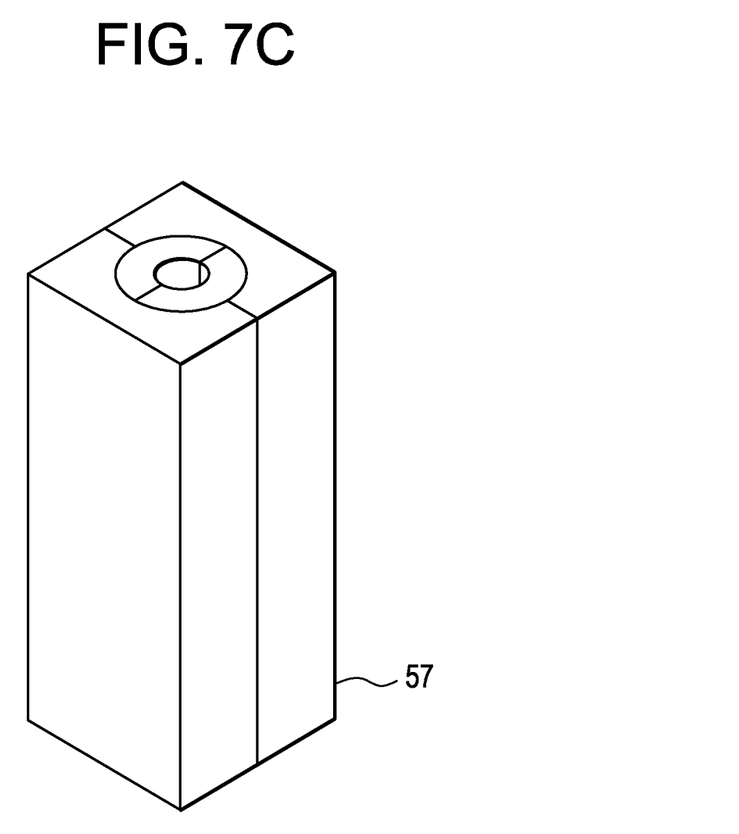

Now referring to FIG. 7a, in one preferred prophetic method of manufacturing the present invention, mold elements 51,52,53,54, and 55 are first created. Now referring to FIG. 7b, mold elements 52,53 and 54 are then assembled to form a subassembly 56. Now referring to FIG. 7c, lastly, mole elements 51 and 55 are combined with the subassembly 56 to form a final mold 57 that is useful for forming the implants of the present invention.

Figure 8A:
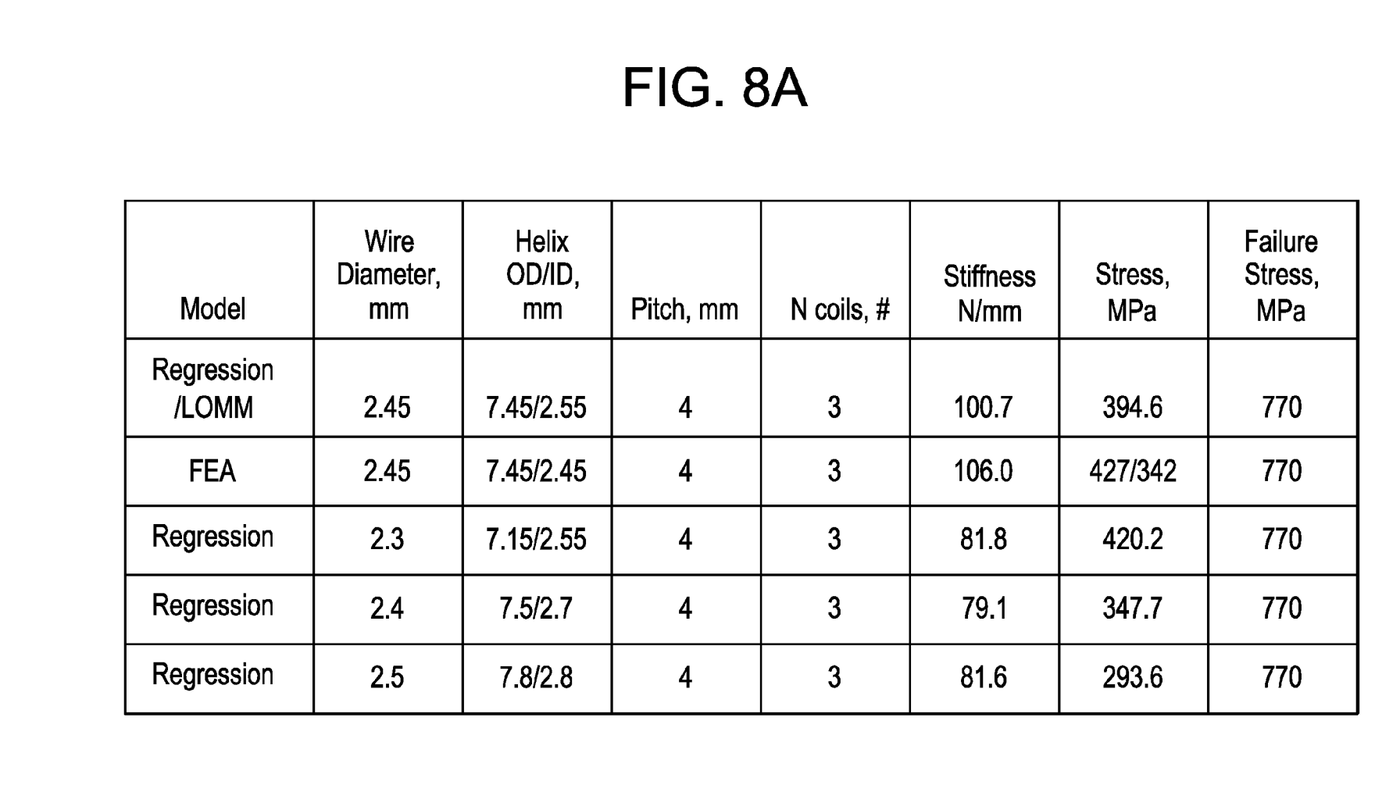
FIG. 8a presents a table of estimated stresses for various embodiments of the present invention.

In an effort to optimize the implant design, a number of variables were modified on the implant design and qualities such as stiffness, stress and failure stress were estimated. Some of the variables modified include wire diameter, helix ID and OD, pitch and the number of coils. FIG. 8a presents a table of estimated stresses for various embodiments of the present invention. The following Regression Equations were used to calculate stiffness and stress:

$$Stiffness = 170.2 + 227.96*WD - 101.95*CD + 12.15*P - 55.62*NC, \text{ and}$$

$$Stress = 1887.19 + 199.19*WD - 369.85*CD + 86.96*P - 159.72*NC,$$

where WD is the wire diameter; CD is the nominal coil diameter ((OD+ID)/2); P is the pitch; and NC in the number of coils.

These results demonstrate that a large wire diameter and a large OD/ID ratios produce favorable stress distributions in the implant.

Figure 8B:
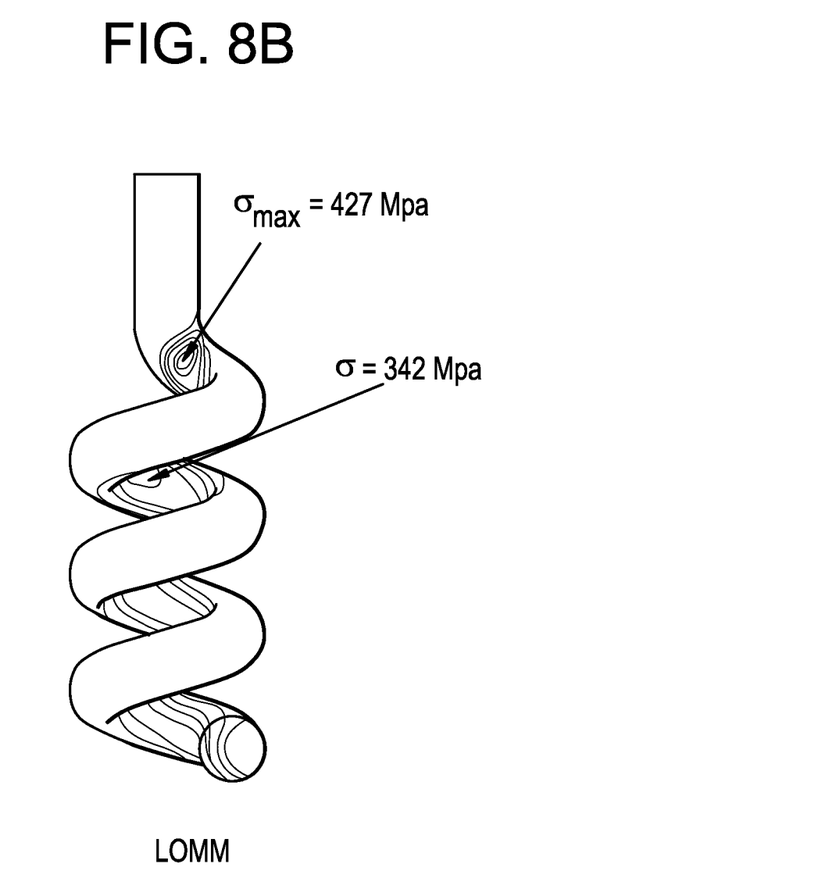
FIG. 8b discloses the major principle stress contour of an embodiment of the present invention.

FIG. 8b discloses the major principle stress contour of an embodiment of the present invention that was considered in the design optimization work presented in FIG. 8a.

One skilled in the art will appreciate that the rod of the device may be configured for use with any type of bone anchor, e.g., bone screw or hook; mono-axial or polyaxial. Typically, a bone anchor assembly includes a bone screw, such as a pedicle screw, having a proximal head and a distal bone-engaging portion, which may be an externally threaded screw shank. The bone screw assembly may also have a receiving member that is configured to receive and couple a spinal fixation element, such as a spinal rod or spinal plate, to the bone anchor assembly.

The receiving member may be coupled to the bone anchor in any well-known conventional manner. For example, the bone anchor assembly may be poly-axial, as in the present exemplary embodiment in which the bone anchor may be adjustable to multiple angles relative to the receiving member, or the bone anchor assembly may be mono-axial, e.g., the bone anchor is fixed relative to the receiving member. An exemplary poly-axial bone screw is described U.S. Pat. No. 5,672,176, the specification of which is incorporated herein by reference in its entirety. In mono-axial embodiments, the bone anchor and the receiving member may be coaxial or may be oriented at angle with respect to one another. In poly-axial embodiments, the bone anchor may biased to a particular angle or range of angles to provide a favored angle the bone anchor. Exemplary favored-angle bone screws are described in U.S. Patent Application Publication No. 2003/0055426 and U.S. Patent Application Publication No. 2002/0058942, the specifications of which are incorporated herein by reference in their entireties.

In some embodiments, the assembly may be implanted in accordance with the minimally invasive techniques and instruments disclosed in U.S. Pat. No. 7,179,261; and US Patent Publication Nos. US2005/0131421; US2005/0131422; US 2005/0215999; US2006/0149291; US2005/0154389; US2007/0233097; and US2005/0192589, the specifications of which are hereby incorporated by reference in their entireties.

We claim:

1. A posterior dynamic spinal stabilization system, comprising:
    a) a rod having a first end portion, an intermediate portion having a substantially helical portion having a centerline, and a second end portion,
    b) a first bone anchor having i) a shank and ii) a rod-receiving portion mated to the first end portion of the rod,
    c) a second bone anchor having i) a shank and ii) a rod-receiving portion mated to the second end portion of the rod, wherein the substantially helical portion of the rod comprises a polymer matrix reinforced with continuous fibers,
    wherein substantially all of the fibers are oriented substantially parallel to the centerline of the helical portion, wherein the rod is modular, and comprises separate intermediate portion and end portions, wherein the intermediate portion comprises a pair of threaded ends having a threadform, and wherein the threaded ends of the intermediate portion each comprise a polymer matrix reinforced with continuous fibers, wherein the fibers are oriented substantially parallel to a contour of the threadform.

2. The system of claim 1 wherein the continuous fibers are carbon fibers.

3. The system of claim 1 wherein at least 50% of the continuous fibers are at least 3 mm in length.

4. The system of claim 1 wherein the polymer matrix comprises a polyarylethyl ketone (PAEK).

5. The system of claim 4 wherein the PAEK is selected from the group consisting of polyetherether ketone (PEEK), polyether ketone ketone (PEKK) and polyether ketone (PEK).

6. The system of claim 5 wherein the PAEK is PEEK.

7. The system of claim 1 wherein the fiber comprises between 10 vol % and 70 vol % of the intermediate portion.

8. The system of claim 1 wherein the intermediate portion has a length $L_I$, at least one end portion of the rod has a length $L_E$, and the $L_E$ is at least 150% of the $L_I$.

9. The system of claim 1 wherein the polymer is selected from the group consisting of polycarbonates, polyesters, (particularly aromatic esters such as polyalkylene terephthalates, polyamides; polyalkenes; poly(vinyl fluoride); PTFE; polyarylethyl ketone (PAEK); and mixtures thereof.

10. The system of claim 1 wherein the fibers are homogeneously extruded.

11. A posterior dynamic spinal stabilization rod having a first end portion, an intermediate portion having a substantially helical portion having a centerline, and a second end portion,
    wherein the substantially helical portion of the rod comprises a polymer matrix reinforced with continuous fibers, wherein the fibers are oriented substantially parallel to the centerline of the helical portion, wherein the rod is modular, and comprises separate intermediate portion and end portions, wherein the intermediate portion comprises a pair of threaded ends having a threadform, and wherein the threaded ends of the intermediate portion each comprise a polymer matrix reinforced with continuous fibers, wherein the fibers are oriented substantially parallel to a contour of the threadform.

12. The system of claim 11 wherein the continuous fibers are carbon fibers.

13. The system of claim 11 wherein at least 50% of the continuous fibers are at least 3 mm in length.

* * * * *